United States Patent [19]
Fuisz

[11] Patent Number: 6,143,742
[45] Date of Patent: Nov. 7, 2000

[54] TREATMENT FOR NECROTIZING INFECTIONS

[75] Inventor: Richard C. Fuisz, McLean, Va.

[73] Assignee: Fuisz Technologies Ltd, Chantilly, Va.

[21] Appl. No.: 09/209,740

[22] Filed: Dec. 11, 1998

Related U.S. Application Data

[60] Provisional application No. 60/069,389, Dec. 11, 1997.

[51] Int. Cl.[7] .......................... A61K 31/535; A61K 31/43; A61K 31/545; A61K 31/495; A61K 31/445
[52] U.S. Cl. ....................... 514/231.5; 514/199; 514/200; 514/252; 514/255; 514/311; 514/474; 514/494
[58] Field of Search ................................. 514/231.5, 252, 514/255, 311, 199, 200, 474, 494

[56] References Cited

U.S. PATENT DOCUMENTS

| | | | |
|---|---|---|---|
| 5,196,438 | 3/1993 | Martin et al. | 514/311 |
| 5,413,999 | 5/1995 | Vacca et al. | 514/231.5 |

FOREIGN PATENT DOCUMENTS

97/02268  1/1997  WIPO .

OTHER PUBLICATIONS

Holder, Ian Alan, "Experimental studies of the pathogenesis of infections due to *Pseudomonas aeruginosa*: effect of treatment with protease inhibitors", Rev. Infect. Dis., 5(Suppl. 5) p. 914–921 (abstr).

Meltzer et al., "Necrotizing Fasciitis: A diagnostic Challenge", American Family Physician, Jul. 1997, pp145–149.

Amy Pakyz and Debra Israel, "Overview of Protease Inhibitors", Journal of the American Pharmaceutical Association, vol. NS37, No. 5, Sep./Oct. 1997, pp 543–551.

*Primary Examiner*—Kevin E. Weddington
*Attorney, Agent, or Firm*—Richard D Schmidt

[57] ABSTRACT

The treatment of for arresting the destructive effects of proteolytic enzymes produced by a host infecting organism, such as "flesh eating bacteria", is carried out using therapy with includes the administration of one or more protease inhibitors.

15 Claims, No Drawings

TREATMENT FOR NECROTIZING INFECTIONS

This application claims the benefit of U.S. provisional application 60/069,389, filed Dec. 11, 1997.

BACKGROUND

Several well publicized incidents have occurred in which patients have contracted virulent forms of common infectious organisms. These organisms (the so-called "flesh eating bacteria"), it is believed, produce proteolytic enzymes and can cause soft tissue infections known as necrotizing fasciitis.

Patients infected with these organisms often experience vascular thrombosis and ischemic gangrene of the underlying tissue in the affected area. Left untreated, the condition spreads rapidly in the body's tissues leading to amputation and, in some cases, death. In addition, diagnosis is difficult because the infection's symptoms often mimic those of cellulitis, a disorder which calls for a very different course of treatment.

The effective treatment of necrotizing fasciitis is often problematic. Conventional treatments involve the use of one or more of: antibiotics, minerals, vitamins, hyperbaric oxygen, surgical abridgement and, as a last resort, amputation. In *American Family Physician*, vol. 56, No. 1, (July, 1997), pages 145–49, Drs. D. L. Meltzer and M. Kabongo describe a necrotizing fasciitis case and discuss a treatment regime which includes a combination of several of these.

It is believed that proteolytic enzyme producing bacteria, such as Streptococci, Staphylococci and *Escherichia coli* organisms, to name a few, are generally responsible for the current increase in incidences of these virulent infections.

*Streptoccus viridans*, a common bacteria, is believed to be one of these virulent, "flesh-eating" bacteria. When *Strep. viridans* is present, the destruction of tissue is mediated via the action of the proteolytic enzyme which the organism has produced.

While proteolytic enzymes are believed to be involved in the action of these bacterial infections, they are not usually treated with protease inhibitors.

Protease inhibitors, along with reverse transcriptase inhibitors (e.g., didanosine and zidovudine), are commonly used to treat patients having compromised immune systems due to retroviral infections, such as human immunodeficiency virus (HIV) and acquired immunodeficiency syndrome (AIDS). U.S. Pat. Nos. 5,196,438 and 5,413,999 discuss the use of the protease inhibitor drugs saquinavir and indinavir to treat retroviruses.

In HIV treatment, protease inhibitors retard the production of HIV protease, the enzyme responsible for processing HIV genes that form protein products when infectious viral particles spread. Thus, protease inhibitors cause the production of immature, noninfectious viral particles and help curb the spread of HIV throughout the host's body. See A. Pakyz and D. Israel, "Overview of Protease Inhibitors", in *Journal of American Pharmaceutical Association*, vol. NS37, No. 5, pages 543–51 (September/October 1997).

While research has been done on their effectiveness in treating HIV and AIDS, the use of protease inhibitors to treat infections other than retroviruses has not been widespread. This invention deals with such use.

The invention provides a simple and effective method of inhibiting the effects of the proteolytic enzymes produced by non-retroviral organisms, while a treatment regimen is worked out to eradicate the organisms in those affected.

SUMMARY OF THE INVENTION

It has now been discovered that protease inhibitors, when given in suitable amounts, can be used to retard the affects of proteolytic enzymes produced by certain strains of necrotizing soft tissue infections, especially necrotizing fasciitis. The protease inhibitors retard the onset of such necrotizing infections by inhibiting the destructive effects of the proteolytic enzymes produced by *Strep. viridans* and other such bacteria.

The invention has many advantages, among them are:

(A) the minimization of the need for more traumatic types of treatments, e.g., amputation;

(B) the use of a currently available therapeutic agents, whose managed dosing has proven effective in managing and arresting the spread of a life-threatening condition;

(C) the provision of a chemical agent which, along with optional supplemental agent(s), arrests the spread of potentially lethal infections; and (D) the use of topical dosage forms, which avoid the gastro-intestinal side effects which can result from the systemic use of protease inhibitors.

These and other advantages will become clear from a consideration of the following specification and claims.

DESCRIPTION OF THE INVENTION

The invention deals with compositions, methods and products for treating/managing the effects of infections of proteolytic enzyme producing organisms on the soft body tissues of hosts. Suitable hosts include human beings in need of treatment for such infections.

The compositions comprise at least one protease inhibitor selected from: indinavir, nelfinavir, ritonavir and saquinavir, and their pharmaceutically acceptable salts and esters and the like. Useful protease inhibitors include indinavir sulfate, saquinavir mesylate and ritonavir.

Protease inhibitors in this application retard the effects of necrotizing proteolytic enzyme infections by binding to the protease active sites, thereby allowing the attending physician time to determine and implement one or more treatment regimens to eradicate the infecting organism, since these organisms generally do not readily succumb to standard antibiotic treatments.

When the protease inhibitors are used in this manner, the need for invasive procedures, such as surgical abridgment and/or amputation is minimal while treatment regimens for the underlying invading organisms are implemented. Preferably, amputation will be unnecessary.

While one or more protease inhibitor(s) can be used alone, supplemental agents and/or techniques and can be used concomitantly with protease inhibitors. The supplemental agents can be one or more selected from the group consisting of: antibiotics, hyperbaric oxygen, minerals and vitamins. Combinations of two or more of these may be used.

By "concomitant" use, applicant means the use of one or more supplement(s) along with, or between, doses of protease inhibitors. Thus, these supplements can be employed at the same time that protease inhibitors are given or in a sequential treatment regimen.

Useful antibiotics include cefazolin, clindamycin, amoxicillin and other suitable members of the cephalosporin family of compounds.

Hyperbaric oxygen is administered by flooding the affected area with gaseous oxygen to inhibit further necrotization by any anaerobes present there. When used at room temperature, oxygen is a gas. Pharmaceutically acceptable gaseous/liquid carriers may be employed.

Minerals, such as zinc, and vitamins, for example vitamin C, can be used in suitable amounts. They are believed to augment the effectiveness of one or more of the other therapeutic agents/techniques by augmenting the body's immune responses.

It is believed that useful therapeutic amounts of protease inhibitors will range from about 800 mg to about 3,000 mg per day. The inhibitors are preferably administered about 2 to about 4 times a day for the prescribed course of treatment, usually periods lasting from about one week up to about several months. Supplemental agents, when used, are administered at dosage levels which enhance the effectiveness of the protease inhibitors. That is, if concomitant use of some supplemental agents is contraindicated, their use may be deferred until use of one or more of the protease inhibitors has ceased.

While gaseous agents are generally used topically, the protease inhibitors used herein can be given to patients in need of treatment using a variety of routes. The most effective routes will be dictated by the site and character of the infection.

Generally, local or topical administration is used when the site of infection is accessible, so that direct application to the site of the protease inhibitor-containing formulations and/or the supplemental agents can be effected. Topical application to epidermal surfaces is preferred.

Topical administration also minimizes the risk of unwanted gastro-intestinal side effects that can be associated with the systemic use of protease inhibitors.

When the site of infection is not accessible, systemic administration is useful. Systemic routes are those in which the protease inhibitors or other agents enter the bloodstream and are carried throughout the body by the circulatory system of the host. Oral, intramuscular and intravenous administration are preferred systemic routes.

Oral dosage contemplated include solid, semisolid and liquid formulations, containing carriers and other ingredients tailored to the final dosage form. Thus, tablets, capsules, dragees, solutions, suspensions and emulsions can be used. Coatings are contemplated.

In some instances, the use of both topical and systemic dosage forms are indicated. For example, an infection involving the ear can be treated with both topical application for the skin surface and oral dosage forms or injections for the inner ear.

The active agents described herein can also be administered via anal, buccal or nasal routes.

The amounts and the nature of the fillers, stabilizers, carriers and other pharmaceutical excipients used along with the protease inhibitors and optional supplements will be dictated by such factors as the route and frequency of administration.

The use of oxygen and other therapies, including protease inhibitors, should be tailored to the patient's needs and be in accord with the sound judgment of his or her physician. All dosage levels recited herein are suggestions, subject to change based on appropriate medical judgment and individual need.

EXAMPLES

The following examples illustrate the invention.

Example 1

Indinavir is given to patients suffering from necrotizing fasciitis by directly applying a topical composition containing 800 mg of the protease inhibitor to epidermal sites of infection for two to three times a day for a period of one to two weeks. Retardation of the effects of the enzymatic destruction of soft body tissues of the patient is found.

Example 2

Indinavir is given to patients suffering from necrotizing fasciitis by intravenous injection of 800 mg of the drug without topical application for two to three times a day for a period of one to two weeks. Similar results to those obtained in Example 1 are is found.

Example 3

Indinavir is given to patients suffering from necrotizing fasciitis by concurrently applying topical compositions containing 400 mg of the protease inhibitor to epidermal sites of infection along with intravenous injections containing 400 mg of the drug for two to three times a day for one to two weeks. Retardation of soft tissue destruction is observed.

Examples 4–6

The procedures of Examples 1 through 3 are repeated with co-administration of the antibiotic cefazolin. Results similar to those of Examples 1–3 are obtained.

Examples 7–9

The procedures of Examples 1–3 are augmented by co-administration of vitamin C and zinc. Benefits similar to those of Examples 1–3 are seen.

Examples 10–12

The procedures of Examples 1–3 are augmented by co-administration of gaseous hyperbaric oxygen. Similar results are observed.

Examples 13–15

Using a procedures similar to those of Examples 1–3, up to 1800 mg daily of sequinavir is given to infected patients. Retardation of the enzymatic destruction of soft body tissues occurs.

Examples 16–18

Using procedures similar to those of Examples 1–3, 600 to 800 mg daily of ritonavir is given to infected patients. Results like those of Examples 1–3 are found.

Examples 19–21

Using procedures similar to those of Examples 1–3, 2250 mg per day of nalfinavir is given to infected patients. Effects similar to those of Examples 1–3 are produced.

The use of larger or smaller quantities of active agents, based upon patient need or other considerations, can be used.

Reasonable variations, such as those which would occur to a skilled artisan, can be made herein without departing from the scope of the invention.

I claim:

1. A composition useful for arresting the destructive effects of proteolytic enzymes produced by a host infecting organism comprising a suitable amount of at least one protease inhibitor.

2. The composition of claim 1 wherein the infecting organism is from the group consisting of Streptococci, Staphylococci and *Escherichia coli*.

3. The composition of claim 2 wherein the protease inhibitor is at least one selected from the group consisting of indinavir, nelfinavir, ritonavir and saquinavir, and their pharmaceutically acceptable salts and esters.

4. A method of arresting the destructive effects of proteolytic enzymes produced by a host infecting organism other than a retrovirus comprising administering to a patient in need thereof an effective amount of at least one protease inhibitor.

5. The method of claim 4 wherein the infecting organism is from the group consisting of Streptococci, Staphylococci and *Escherichia coli*.

6. The method of claim 5 wherein the protease inhibitor is at least one selected from the group consisting of indinavir, nelfinavir, ritonavir and saquinavir, and their pharmaceutically acceptable salts and esters.

7. A method of treating a protease meditated infection other than a retrovirus comprising administering to a patient in need thereof a therapeutic amount of at least one protease inhibitor.

8. The method of claim 7 wherein the infection is a skin infection.

9. The method of claim 8 wherein the administration is carried out by at least one route selected from topical and systemic routes.

10. The method of claim 9 wherein the administration is topical.

11. A method of treating a protease mediated infection other than a retrovirus comprising administering to a patient in need thereof a therapeutic amount of at least one protease inhibitor and, concomitantly, at least one supplemental agent.

12. The method of claim 11, wherein the supplemental agent is an antibiotic, hyperbaric oxygen, one or more minerals, or one or more vitamins.

13. The method of claim 11, wherein the antibiotic is one or more from the group consisting of cefazolin, clindamycin, amoxicillin or other cephalosporins.

14. The method of claim 11, wherein the supplemental agent is Vitamin C.

15. The method of claim 11, wherein the supplemental agent is zinc.

* * * * *